United States Patent [19]

Ader et al.

[11] Patent Number: 4,756,556
[45] Date of Patent: Jul. 12, 1988

[54] EASILY MANIPULATED BOOK

[76] Inventors: Judith L. Ader, 1374 Pine Valley Dr.; Shirley C. Browne, 11830 Donlin Dr., both of West Palm Beach, Fla. 33414

[21] Appl. No.: 31,774

[22] Filed: Mar. 30, 1987

[51] Int. Cl.[4] .................. B42D 1/00; B48D 5/00; G09D 3/00; G09F 19/00

[52] U.S. Cl. ..................... 281/15 A; 281/15 R; 40/107; 40/530

[58] Field of Search ............. 281/15 A, 15 R, 19 A, 281/45, 48, 49, 50, 63 R; 434/429, 167; 40/1, 19, 5, 107, 617, 530, 533; 446/147

[56] References Cited

U.S. PATENT DOCUMENTS

| | | | |
|---|---|---|---|
| 1,002,639 | 9/1911 | Broussard | 281/15 R |
| 1,548,248 | 8/1925 | Binns et al. | 281/15 A |
| 2,501,902 | 3/1950 | Howell | 446/147 |
| 3,275,316 | 8/1966 | Cleary, Jr. | 281/15 R |
| 3,793,758 | 2/1974 | Feldhusen et al. | 40/107 |
| 3,797,146 | 3/1974 | Holes | 281/15 R |
| 3,956,836 | 5/1976 | Seaborn | 40/530 |
| 4,078,325 | 3/1978 | Valentine | 40/530 |
| 4,616,851 | 10/1986 | Mann | 281/15 A |

Primary Examiner—E. R. Kazenske
Assistant Examiner—Paul M. Heyrana, Sr.
Attorney, Agent, or Firm—Alvin S. Blum

[57] ABSTRACT

A book structure is disclosed that is much easier to use than books of conventional construction. It can be used by individuals with impaired motor function and by young children who have not yet developed sufficient coordination to manipulate the pages of a conventional book. Each leaf of the book is of a rigid plastic construction with projections above and below the plane of the leaf for holding printed matter on cards. The projections also serve as spacers to separate the pages from one another to facilitate grasping a selected page. Each page further has a rigid tab projection to serve as a handle. A binder assembly permanently holds the leaves for easy turning and to lie flat at any opened page. The binder includes a handle for easier carrying. The assembly is of a smooth, non-toxic plastic material that resists destruction by young children. The printed matter cards may be replaced with new editions as required without the expense of binding each edition, since the book assembly is reusable.

20 Claims, 3 Drawing Sheets

EASILY MANIPULATED BOOK

This invention relates to the structure of books, and more particularly to a book that can be more easily manipulate by a handicapped person or a young child who is not yet sufficiently coordinated to handle a book of conventional construction.

BACKGROUND OF THE INVENTION

In the conventional construction of books, pages printed with text, pictures, and the like are bound together with covers along one common edge which is reinforced to form a spine. The binding is so constructed that the book may be opened between any two pages for use. Spiral wires, ring binders and the like may be employed to permit laying open the book at a selected page. Index tabs projecting from the edge of each page may be useful for opening to a particular page. Children's books may be made of a heavier card stock for easier page turning. Nonetheless, considerable dexterity is required to open a book and turn the pages. The fingers must be able to reach between and separate the pages, grasp a selected page and turn it without tearing, wrinkling or pulling it from its binding. Unsteady hands may be unable to carry a conventional book. Books are easily torn, stained, chewed and otherwise destroyed by young children at play. Nevertheless, very young children can benefit from the use of books and especially when they can handle them personally, because they combine the pleasurable experience of a personal toy with the educational experience of books. However, they are not sufficiently coordinated to use books of conventional construction effectively.

Handicapped persons may retain greater independence if they have access to book information. However, books of conventional constructon cannot be used effectively by many persons afflicted with cerebral palsey, parkinsonism and other motor disorders, whose mental function is unimpaired.

SUMMARY OF THE INVENTION

It is, accordingly, an object of the invention to provide a book that can be manipulated by unsteady hands.

It is a further object to provide a book having spaces between individual leaves for easy insertion of fingers for page turning.

It is a further object to provide rigid, wrinkle and tear-proof leaves.

It is a further object to provide a handle for each leaf.

It is a further object to provide a carrying handle for the book.

The invention comprises a book with a plurality of substantially rigid leaves. Each leaf has an isolated handle projecting from an outer edge. Each leaf has perforations along an inner edge. A common spine includes a carrying handle and rings engaging the perforations in the leaves to bind the leaves together while providing easy opening motion between leaves. Each leaf has surface projections on both faces or pages. These surface projections serve two purposes: 1. they maintain a space between individual leaves to facilitate page turning. 2. they engage the sheets of printed matter to hold them against the surface of the leaf. In this manner, a single book structure may be used for a plurality of applications. As a child matures, the subject matter held in the projections on the leaves may be discarded and replaced by more advanced subject matter. And the same structure may be used for children and the handicapped.

These objects and other will become apparent to those skilled in the art from the following disclosure of the preferred embodiment of the invention taken in conjunction with the accompanying drawings wherein like reference characters refer to similar parts throughout the several views and in which:

BRIEF DESCRIPTION OF THE DRAWINGS

FIG. 7 is a detail of the fastener portion of FIG. 3.

DESCRIPTION OF THE PREFERRED EMBODIMENT OF THE INVENTION

The holders for the printed pages are referred to as leaves, and the printed matter cards are referred to as sheets. In the final assembly, each sheet forms one page of the book.

Figure 1:
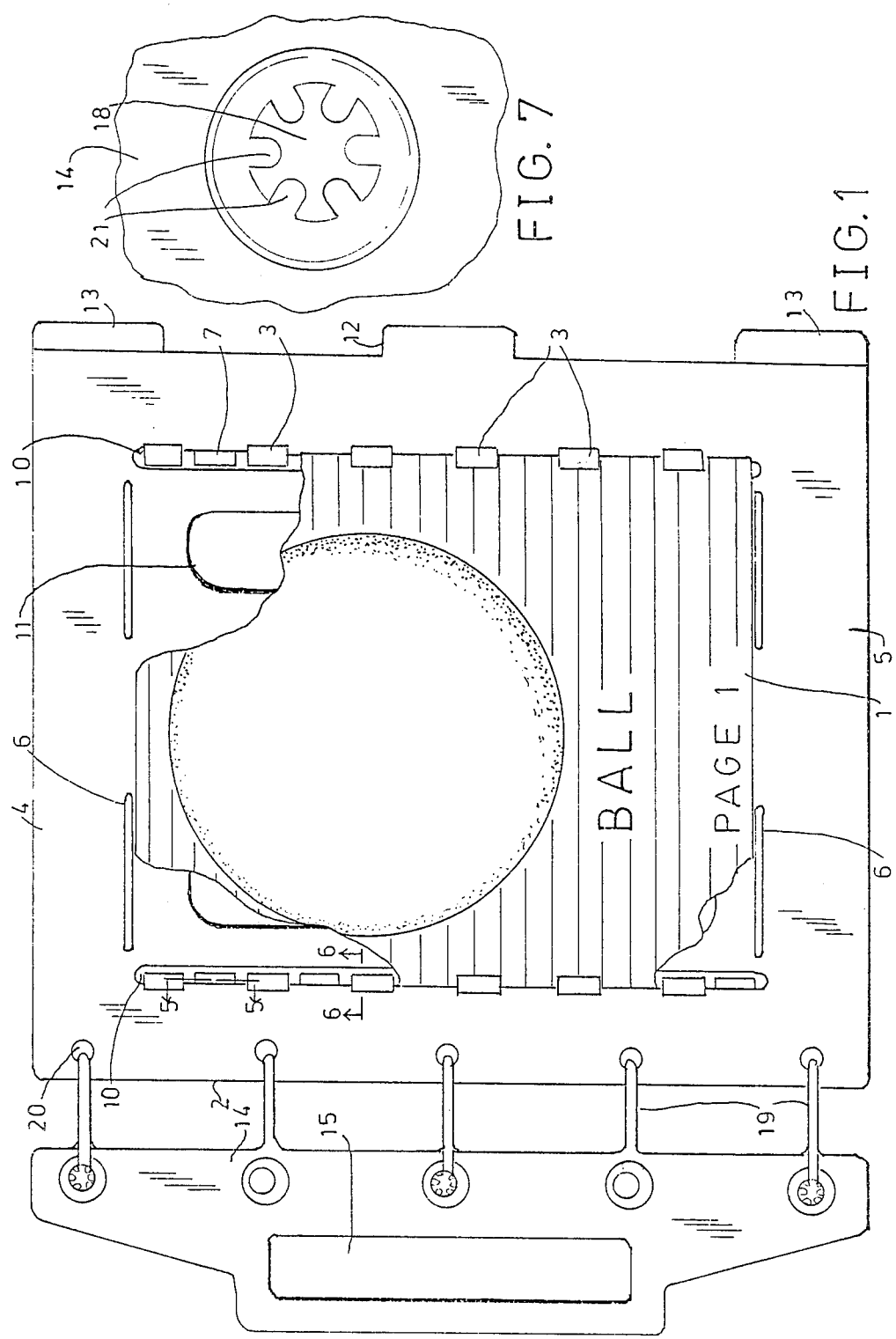
FIG. 1 is a plan view of the book assembly.
Figure 2:
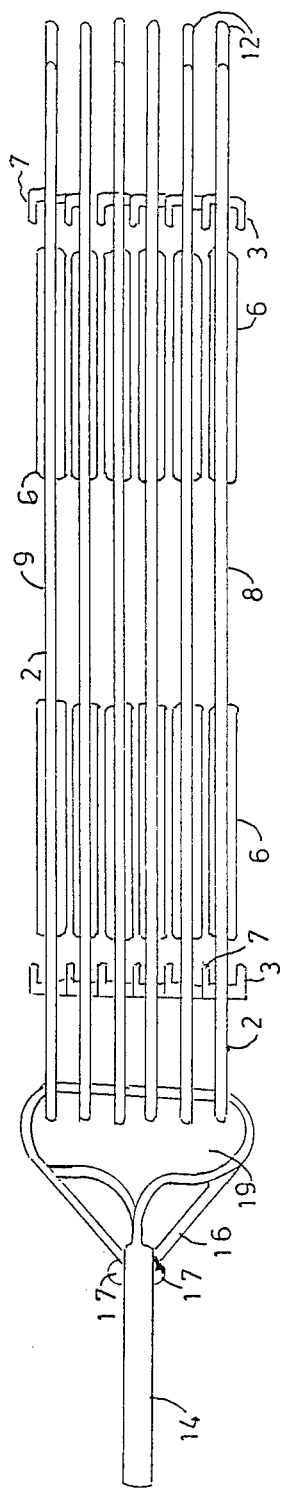
FIG. 2 is an end view of the book assembly.
Figure 5:
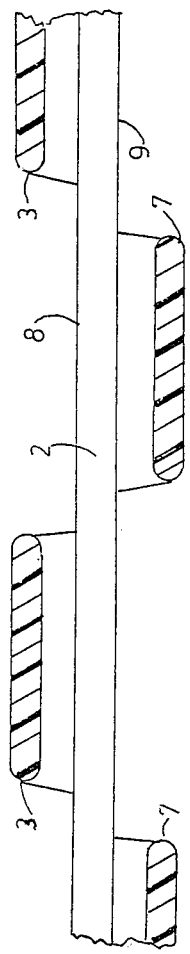
FIG. 5 is a view along line 5—5 of the leaf of FIG. 1.
Figure 6:
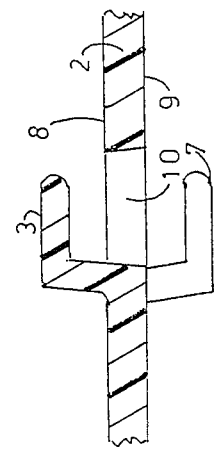
FIG. 6 is a view along line 6—6 of the leaf of FIG. 1.
Figure 3:
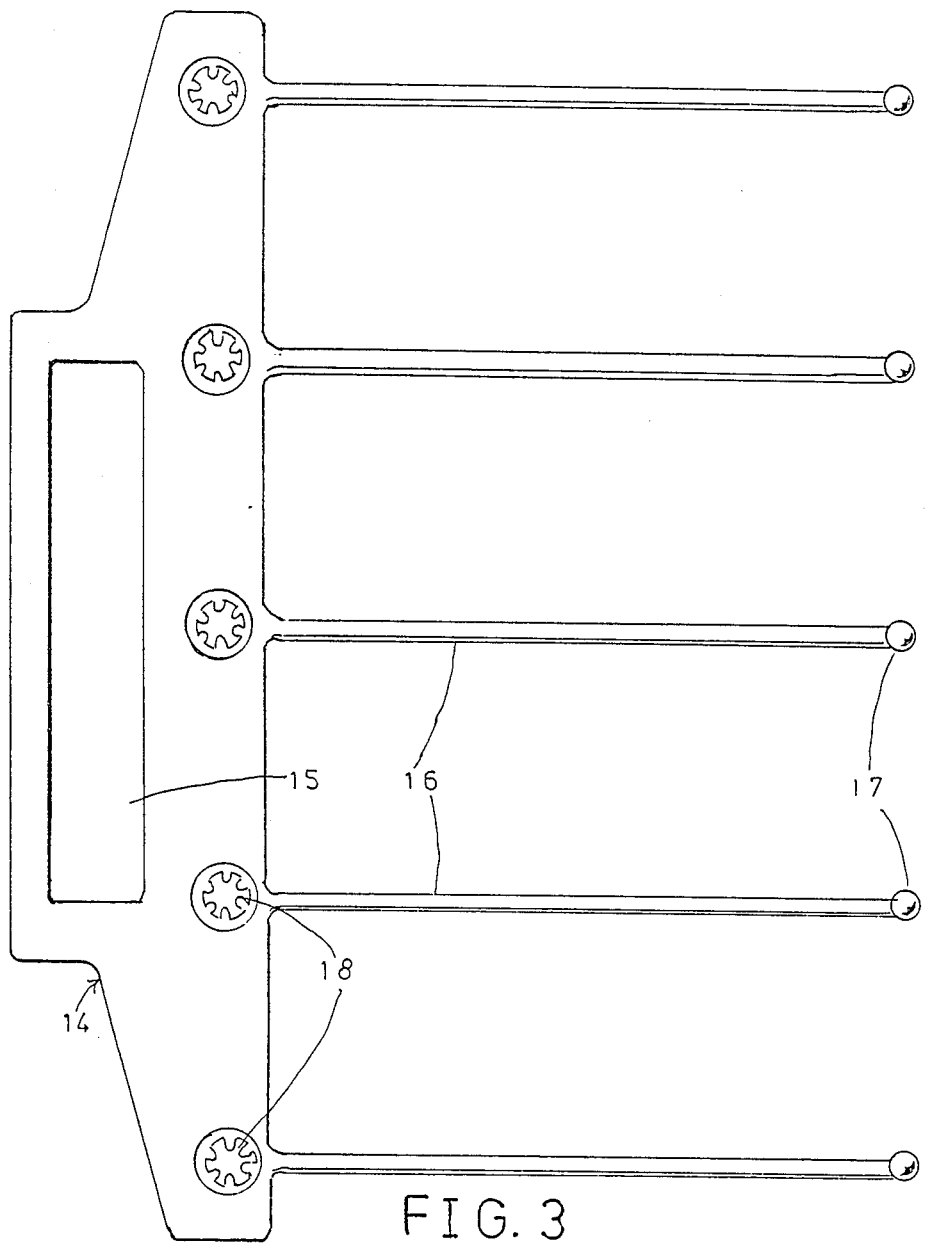
FIG. 3 is plan view of the binder/handle member.
Figure 4:
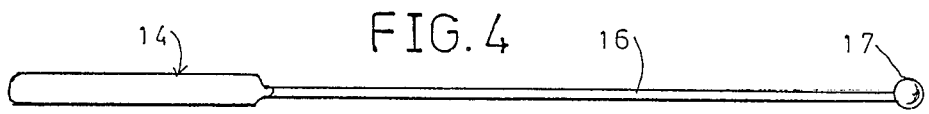
FIG. 4 is an end view of the binder/handle member.

Referring now to the drawings, FIG. 1 shows the book assembly of the invention as it would generally appear to the reader looking at page 1. A printed sheet of heavy paper or cardboard 1 is shown partially broken away to reveal the structure of the underlying leaf 2 that is molded of a relatively stiff, non-toxic plastic such as polypropylene. The printed sheet 1 is held firmly in place on leaf 2 by the projecting holders 3 extending upwardly and inwardly from the surface of leaf 2. The sheet 1 slides in from the top 4 or the bottom 5 of the leaf and the raised projections 6 hold the sheet in place at its top and bottom. As shown in FIGS. 2, 5 and 6, the holders 3 extend above the first surface 8 of the leaf 2 for holding a first printed sheet 1 against the first surface 8 and a second set of holders 7 extend above the second surface 9 for holding a second printed sheet against the second surface 9. The holders 3 and 7 originate from a common edge of an aperture 10 and alternate with each other so that the leaf can be molded in one piece with a simple molding operation where the two halves of the mold open and close in a straight line. Perforations 11 may be formed in leaf 2 to reduce the weight and cost. A tab 12 extends from the outer edge of leaf 2 to make it easy to grasp the page and turn it. Other tabs 13 on other leaves may be staggered to further facilitate grasping. The holders 3,7 and projections 6 extending from the surface of the leaves further facilitate turning of the leaves by spacing the leaves apart from one another as seen in FIG. 2. The member 14 shown in FIGS. 3, 4 and 1 combines the functions of a carrying handle with a hand-engaging aperture 15 for easy carrying of the book along with a spine or binding means for holding the individual leaves in a manner that permits the book to be opened to any page without significant resistance from the binding means. Member 14, FIG. 3 is molded in one piece in a simple mold. The rod-like extensions 16 have a generally circular or oval cross section, terminating in spheres 17. Locking apertures 18 (FIGS. 7, 3) are designed so that the extensions 16 may be bent around into loops 19 (FIG. 2) and the spheres 17 forced through the apertures. The flaps 21 encircling the aperture 18 are thinner towards the center of the aperture. These flaps snap around the sphere 17 after it passes through the aperture and lock it in place. The rod-like extensions 16 are first passed through the holes 20 in the leaves and then locked into the locking apertures 18 to permanently lock the leaves 2 to the binder member 14. Other securing means well known in the art such as snap locks, welding and cementing may be employed for securing the end of extensions 16. The member 14 substantially flat and the leaves 2 turn freely in the loops 19 formed from the extensions 16. This structure yields substantial less resistance to turning the pages than conventional bindings and the books will lie flat when opened to any page. Furthermore, the leaves cannot be torn out. The constructon is virtually indestructable, as compared to conventional book structures. Because this book assembly is a carrier for the printed matter, the many editions of printed matter can be produced without binding costs. And a single model or "edition" of the instant invention may be produced for all the printed matter editions. The cost of a single book assembly may be amortized over many editions of printed matter of increasing content as a child matures, for example. Each leaf of the book may be molded in plastic of a different color to further distinguish each one. The molded surfaces are smooth and rounded and of a non-toxic, very strong plastic such as polypropylene to withstand the destructive forces of children and to present less hazard to children. By design, each of the molded parts that make up the book assembly are too large to be swallowed by even the most voracious of omnivorous users.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

What is claimed is:

1. A book assembly for holding a plurality of printed pages in book form that can be easily manipulated by handicapped users and uncoordinated children, comprising:
   a. a plurlity of molded leaves, each of said leaves having a first broad surface and a second, opposite broad surface;
   b. printed-matter sheet holding means for removably holding a sheet of printed matter on a surface;
   c. each of said leaves having a first set of said sheet holding means on said first surface and a second set of said sheet holding means on said second surface to hold a first printed page on said first surface and a second printed page on said second surface;
   d. leaf-binding member means binding said plurality of leaves thereto in a manner permitting said leave to be freely turned and said book assembly to lie open at any selected page;
   e. said holding means extending above said surfaces of said leaves to separate said leaves from one another to facilitate grasping each of said leaves individually for page turning; and
   f. said holding means including means for engaging only the marginal edge portions of the outer face of said sheet when the inner face of said sheet is engaged by said surface of one of said leaves to thereby hold said sheet between said holding means and said one of said leaves.

2. In the book assembly of claim 1, said leaves having a substantially rigid construction to facilitate sheet holding and page turning.

3. In the book assembly of claim 2, said leaves further including a projecting tab means extending from an edge of each leaf for grasping when turning pages.

4. In the book assembly of claim 2, said binding member means including handle means for more easily carrying said assembly.

5. In the book assembly of claim 4, said handle means include a hand-engaging aperture.

6. In the book assembly of claim 2, said leaf-binding member means including a plurality of leaf-engaging, elongate projections extending from a common body, said projections having locking terminations, and said common body including a plurality of termination securing means for securing said terminations for forming a plurality of leaf-engaging loops, and each of said leaves including a plurality of loop-engaging apertures for binding said leaves to said binding member.

7. In the book assembly of claim 6, said leaves and said leaf-binding member means each molded in one piece of a strong, non-toxic composition to provide pieces too large to swallow and safe to chew upon.

8. In the book assembly of claim 7, the composition is a polyolefin thermoplastic.

9. In the book assembly of claim 7, each of said leaves is molded of a different color to enhance the educational function of the device.

10. In the book assembly of claim 1, said holding means further comprising a plurality of angled projections extending firstly upwardly from the leaf surface and extending secondly parallel to said leaf surface over a fenestration in said surface, said angled projections aligned in two parallel rows, said rows spaced apart sufficiently to engage opposite edges of said printed-matter sheet and said first set and said second set disposed in alternating locations down each row so that each of said leaves may be molded in a simple molding operation with a direct opening and closing of a mold.

11. In the book assembly of claim 10, said holding means further including simple projections extending upwardly from said surface arranged to engage the two edges of said sheet not engaged by said angled projections.

12. A book assembly for holding a plurality of printed pages in book form that can be easily manipulated by handicapped users and uncoordinated children and in a form wherein said printed pages can be readily replaced, comprising:
   a. a plurality of molded leaves, each of said leaves having a broad first surface and a second, opposite broad surface;
   b. printed-matter sheet holding means for removably holding a sheet of printed matter on a surface;
   c. each of said leaves having a set of said sheet holding means on said first surface for holding a printed page on said first surface;
   d. leaf binding means binding said plurality of leaves thereto in a manner enabling said leaves to be turned freely and said book assembly to lie open at any selected page;
   e. said holding means extending above said surfaces of said leaves to separate said leaves from one another to facilitate grasping each of said leaves individually for page turning; and f. said holding means including means for engaging only the marginal edge portions of the outer face of said sheet when the inner face of said sheet is engaged by said surface of one of said leaves to thereby hold said sheet between said holding means and said one of said leaves.

13. In the book assembly of claim 12, said leaves having a substantially rigid construction to facilitate sheet holding and page turning.

14. In the book assembly of claim 12, said leaves further including a projecting tab means extending from an edge of each leaf for grasping when turning pages.

15. In the book assembly of claim 12, said binding means including handle means for more easily carrying said assembly.

16. In the book assembly of claim 12, said handle means include a hand-engaging aperture.

17. In the book assembly of claim 12, said leaf-binding means including a plurality of leaf-engaging, elongate projections extending from a common body, said projections having locking terminations, and said common body including a plurality of termination securing means for securing said terminations for forming a plurality of leaf-engaging loops, and each of said leaves including a plurality of loop-engaging apertures for binding said leaves to said binding member.

18. In the book assembly of claim 12, said holding means further comprising a plurality of angled projections extending firstly upwardly from the leaf surface and extending secondly parallel to said leaf surface, said angled projections aligned in two substantially parallel rows, said rows spaced apart sufficiently to engage opposite edges of said printed-matter sheet.

19. In the book assembly of claim 18, said holding means further including projections extending upwardly from said surface arranged to engage the two edges of said sheet not engaged by said angled projections.

20. In the book assembly of claim 19, said leaves and said leaf binding means each molded in one piece of a strong, non-toxic composition to provide pieces too large to swallow and safe to chew upon.

* * * * *